United States Patent [19]

Ross

[11] Patent Number: 4,850,560
[45] Date of Patent: Jul. 25, 1989

[54] ADJUSTABLE HANGER

[75] Inventor: Stephen O. Ross, Del Mar, Calif.

[73] Assignee: Fisher Scientific Company, Pittsburgh, Pa.

[21] Appl. No.: 279,218

[22] Filed: Dec. 2, 1988

[51] Int. Cl.⁴ .............................................. A47F 1/10
[52] U.S. Cl. ................................ 248/295.1; 248/125; 248/307; 403/166; 403/347
[58] Field of Search .................. 248/295.1, 297.3, 296, 248/307, 311.3, 322, 327, 125, 122, 157; 211/107, 117; 403/166, 347

[56] References Cited

U.S. PATENT DOCUMENTS

| | | | |
|---|---|---|---|
| 3,132,832 | 5/1964 | Kore, Jr. | 248/307 |
| 3,533,583 | 10/1970 | Azim | 248/125 |
| 4,034,438 | 7/1977 | Csokasy et al. | 403/166 X |
| 4,250,647 | 2/1981 | Woodard | 248/297.3 X |
| 4,508,302 | 4/1985 | Hausser | 248/297.3 |
| 4,671,477 | 6/1987 | Cullen | 248/122 |
| 4,706,368 | 11/1987 | Crissman, III et al. | 248/122 X |

Primary Examiner—Ramon O. Ramirez
Attorney, Agent, or Firm—Nydegger & Harshman

[57] ABSTRACT

An adjustable hanger includes an arm having a suspension member, and having an opening for receiving a hanger support frame. A plunger is slidably mounted on the arm, and has a corresponding opening for receiving the hanger support frame. The plunger is slidable to an unlocked position in which the opening in the plunger is aligned with the opening in the arm to allow the arm and plunger to move freely along the hanger support frame through the aligned openings, and a biasing element is interposed between the arm and the plunger for biasing the plunger against the support frame for locking the adjustable hanger in a desired position.

In a preferred embodiment, the plunger is coaxially movable within an axial cavity of the arm, and the plunger includes a button at one end thereof. The arm may include a finger tab, and the suspending member may be in the form of a hook which includes a finger support portion.

11 Claims, 4 Drawing Sheets

ADJUSTABLE HANGER

BACKGROUND OF THE INVENTION

This invention relates generally to adjustable hangers. More specifically, the present invention relates to an adjustable hanger which can be used in a hospital or related medical services environment. The present invention is particularly, though not exclusively, useful for hanging a fluid source, such as an intravenous solution (I.V.) bag at a height which is readily adjustable.

DISCUSSION OF THE PRIOR ART

There are many devices available in the prior art for hanging fluid sources for use in a hospital environment. Typically, I.V. bags and other fluid sources are suspended by a hook or other clamping mechanism which is permanently fixed in its relative height position on a hanger supporting frame. The hook or other suspending mechanism is typically located at a height above a patient lying in a typical hospital bed so that the fluid is infused to the patient from the fluid source by gravity or some mechanical means. The height of the hook is typically permanently fixed onto the hanger support frame so that the height is not readily adjustable. Consequently, different heights are obtained only by utilizing different supporting frames of different overall heights. However, the adjustment, if any, provided in such conventional prior art hanging devices is difficult to manipulate, and not easy and convenient to use. Additionally, the time it takes for a medical staff practitioner to adjust the height may be longer than desired. Making such height adjustments takes staff time which adds up quickly for the many patients requiring such devices, and in turn, adds significant costs to delivery of medical services. In addition, in times of emergency needs, too much lost time can mean the difference between life and death.

In light of the above, the present invention recognizes the need for a hanger which is quickly and easily adjustable. Further, the present invention recognizes the need for an adjustable hanger which is simple and efficient to use, and economical to manufacture yet is reliable in operation.

Accordingly, it is an object of the present invention to provide an adjustable hanger which is simple in operation and allows quick adjustment in the height of the hanger, yet which is effective for accomplishing the task of providing a stable platform from which fluid sources may be hung.

It is another object of the present invention to provide an adjustable hanger which is inexpensive to manufacture, yet reliable and durable in construction.

It is yet another object of the present invention to provide an adjustable hanger which conveniently provides a multitude of adjustment options.

SUMMARY OF THE INVENTION

An adjustable hanger includes an arm having a suspension member, and having an opening for receiving a hanger support frame. A plunger is slidably mounted to the arm, and has a corresponding opening for receiving the hanger support frame. The plunger is slidable to an unlocked position in which the opening in the plunger is aligned with the opening in the arm to allow the arm and plunger to move freely along the hanger support frame through the aligned openings. A biasing element is interposed between the arm and the plunger for biasing the plunger out of the unlocked position and against the support frame for locking the adjustable hanger in a desired position.

In a preferred embodiment, the plunger is coaxially movable within an axial cavity of the arm. Movement of the plunger into the unlocked position is accomplished by pressing on a button at one end of the plunger. The arm may include a finger tab to facilitate pressing the button and the suspending member may be in the form of a hook which includes an additional finger support portion.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
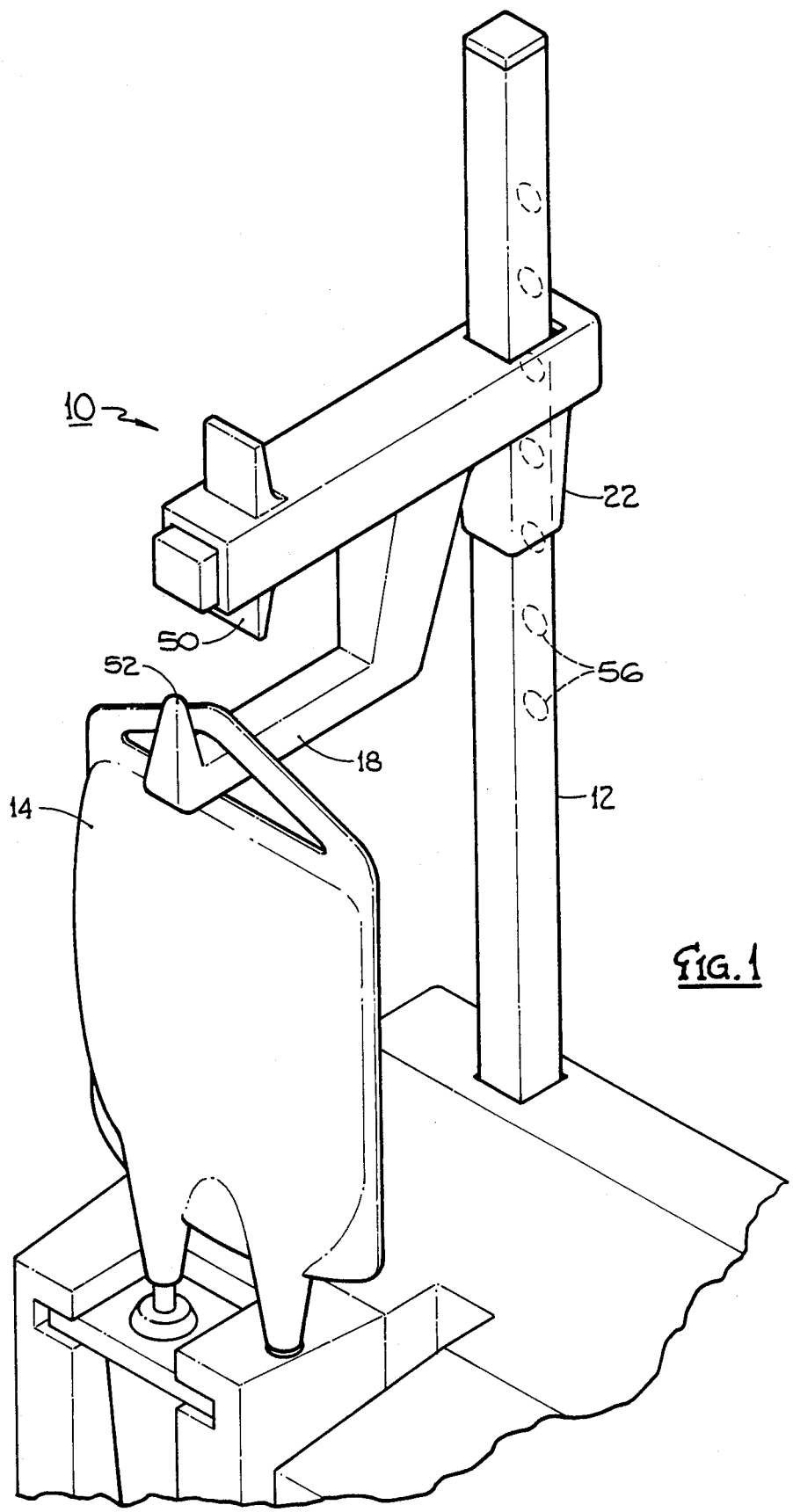
FIG. 1 is a perspective view of one embodiment of the adjustable hanger in use.

Referring intially to FIG. 1, there is shown the adjustable hanger generally designated 10. The adjustable hanger is adjustable in its positioning along a hanger support frame 12, for adjustably controlling the height of the hanger 10 for hanging a fluid source 14 containing medical solutions for delivery to a patient.

Figure 2:
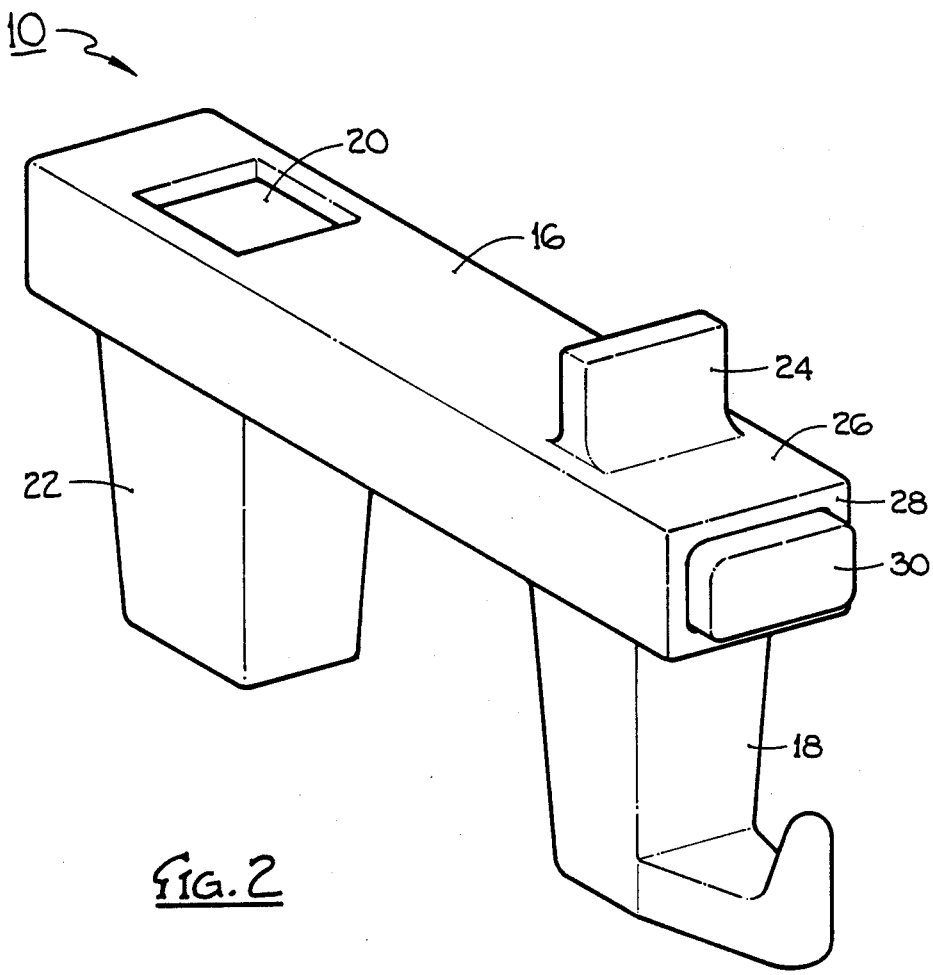
FIG. 2 is a perspective view of an alternative embodiment of the adjustable hanger.

Referring now to FIG. 2, the adjustable hanger 10 comprises an arm 16 having a suspending member 18 for suspending a fluid source 14. In the embodiment shown, the suspending member 18 is in the form of a hook, but could comprise a clamp or other suitable hanging mechanism. The arm further includes an opening or passage 20 for receiving the hanger support frame 12. The shape and size of the passage 20 is adapted to allow the arm 16 to move freely along the hanger support frame 12. The arm 16 has a reinforcing portion 22 which provides added strength to the arm 16 in supporting the weight of the fluid source 14 on suspending member 18. Arm 16 also includes a finger tab 24 on the top side 26 of arm 16.

Figure 3:
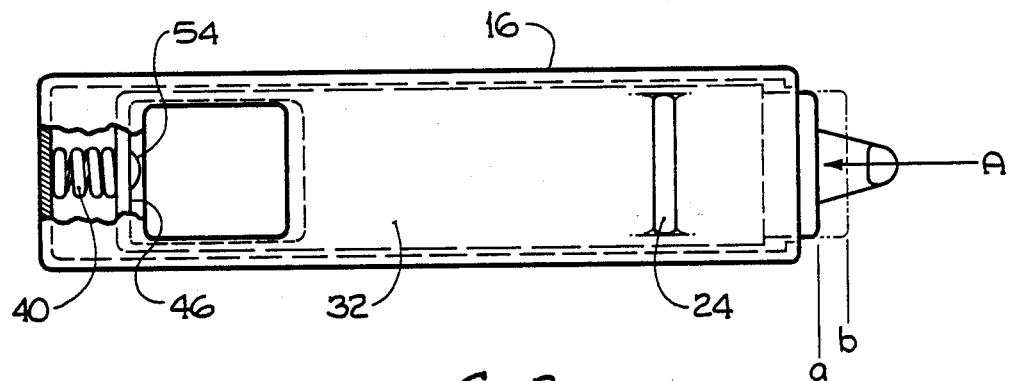
FIG. 3 is a top plan view of the adjustable hanger shown in FIG. 2.
Figure 4:
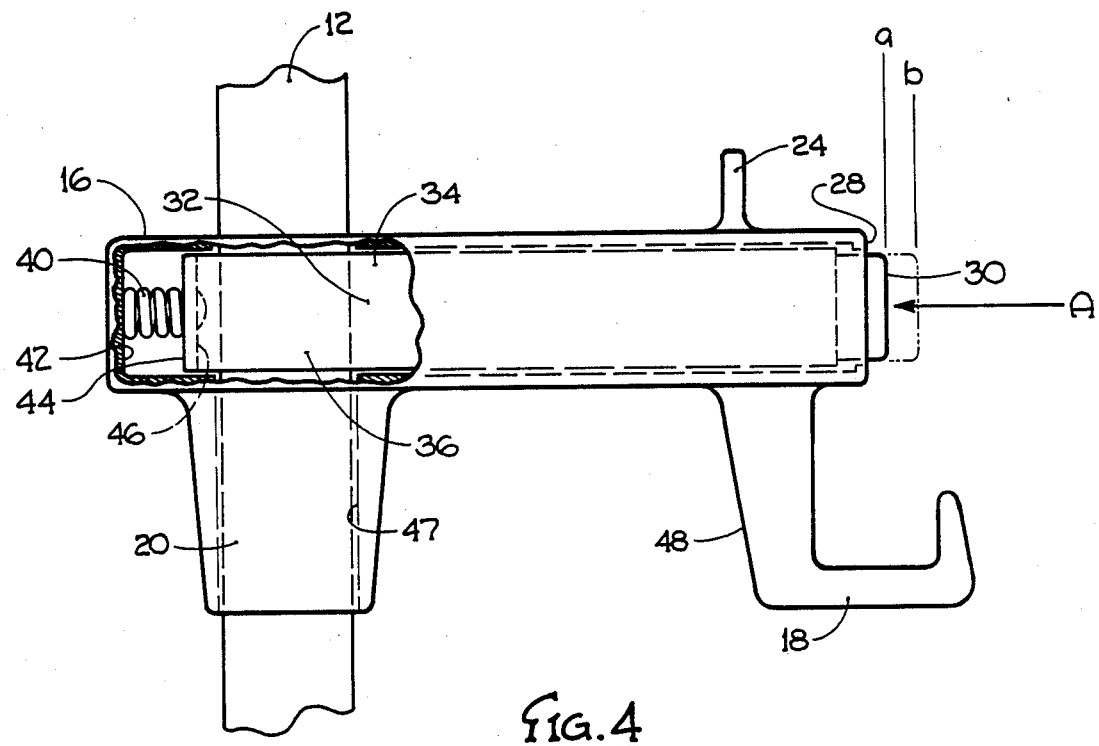
FIG. 4 is side elevational view of the adjustable hanger shown in FIG. 2.
Figure 5:
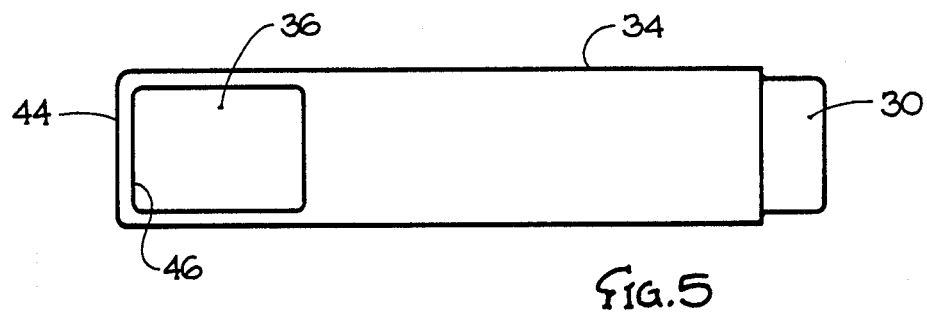
FIG. 5 is a top plan view of the plunger of the adjustable hanger shown in FIG. 2 in accordance with the present invention.
Figure 6:
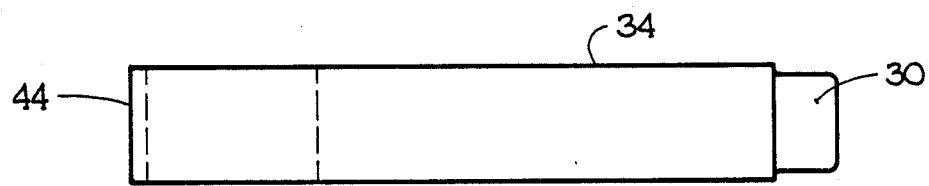
FIG. 6 is a side elevational view of the plunger shown in FIG. 5.
Figure 7:
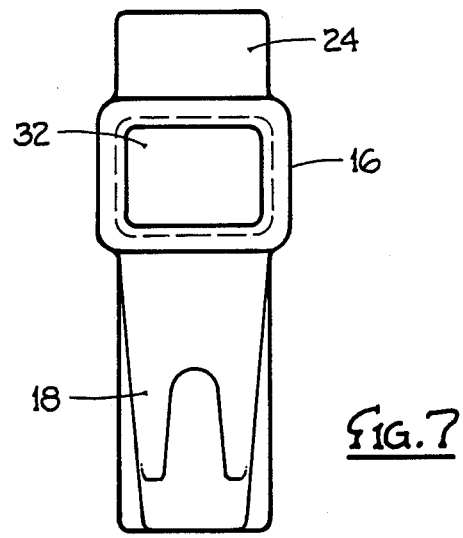
FIG. 7 is an end elevational view of the arm of the hanger shown in FIG. 2.

Protruding from one end 28 of arm 16 is an actuation member 30, which may be in the form of a button as shown. Referring further to FIGS. 3, 4 and 7, the arm 16 has an axial chamber 32 extending the length of arm 16. The axial chamber 32 is of a shape adapted to receive a plunger 34 being slidably mounted in axial chamber 32. As shown in FIG. 5, plunger 34 has a corresponding passage 36 for also receiving hanger support frame 12.

Referring further to FIGS. 3 and 4, plunger 34 is inserted within axial chamber 32 of arm 16. Plunger 34 is of sufficient length so that plunger 34 cooperates with actuation member 30 which protrudes from end 28 of arm 16 to allow actuation of the device. Disposed in axial chamber 32 is a biasing element 40, such as a coil spring as shown, or a leaf spring or other appropriate biasing element. Biasing element 40 is interposed between closed end 42 of arm 16, and plunger end 44, to apply a force opposite to the direction of arrow A, as shown in FIGS. 3 and 4.

OPERATION

In operation, passage 20 of arm 16 and corresponding passage 36 of plunger 34 are aligned so that the adjustable hanger 10 can move freely along hanger support frame 12. The alignment is accomplished by pressing actuation member 30 in a direction generally designated as A in FIG. 4, thus moving plunger 34, so that a locking surface 46 of plunger 34, and inner surface 74 of arm 16 are disengaged from hanger support frame 12, as shown in position "a" of FIGS. 3 and 4. Once the desired height position adjustment has been reached, the user releases the pressure maintained on actuation member 30 so that biasing element 40 urges plunger 34 in a direction opposite to the direction, shown by arrow A, to position "b" as shown in FIGS. 3 and 4. This engages locking surface 46, and inner surface 47, against hanger support frame 12 and thereby locks the adjustable hanger 10 in the desired position. As an aid in the actuation of the plunger 34, the finger tab 24 can be grasped with the index finger, the middle finger can be wrapped around surface 48 on the back side of suspending member 18, and the actuation member 30 can easily be depressed with the thumb. This allows quick actuation of the device and convenient adjustment to the height position as desired. This speed can be critical in a hospital situation where time is at a premium. In addition, the height can be adjusted to any height needed along hanger support frame 12. Ease of actuation can reduce overall time and expense of servicing the patient, which results in lower overall health care costs. It can be appreciated by those skilled in the art that the locking surface 46, and/or inner surface 47, can have serrations or the like to make a more secure locking or clamping engagement against hanger support frame 12. In addition, a projection 54 can be formed on locking surface 46 of plunger 44 substantially as shown in FIG. 3 which will selectively interact with depressions 56 on the back of pole 12 to hold adjustable hanger 10 on support frame 12. It will be appreciated that other locking mechanisms known in the art can be utilized if desired.

In the alternative embodiment shown in FIG. 1, the suspending member 18 is recessed, and in lieu of the surface 48 of suspending member 18 there is a lower finger tab 50. In addition, the suspending member 18 includes an elongated hook portion 52 for ease of mounting the fluid source 14. In addition, in order to save materials, the reinforcing member 22 is of a shorter length than that shown in the embodiment of FIG. 2.

While the particular adjustable hanger as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An adjustable hanger for supporting a fluid source, comprising:
    arm formed with a suspending member engageable with the fluid source, and having a passage for slidably receiving a hanger support frame;
    a plunger slidably mounted on said arm and having a passage alignable with said arm passage, said plunger being slidable to an unlocked position wherein said plunger passage is aligned with said arm passage to allow said arm and plunger to move freely along said hanger support frame; and
    a biasing element interposed between said arm and said plunger for biasing said plunger against said support frame to lock said adjustable hanger in a desired position on said hanger support frame.
2. An adjustable hanger as recited in claim 1, wherein said arm includes an axial cavity within which said plunger is coaxially movable.
3. An adjustable hanger as recited in claim 2, wherein said plunger includes a button at one end thereof, which protrudes from said cavity at one end of said arm.
4. An adjustable hanger as recited in claim 3, wherein said arm includes a finger tab positioned on a top side thereof.
5. An adjustable hanger as recited in claim 4, wherein said suspending member includes a finger support portion positioned on the bottom side of said arm.
6. An adjustable hanger as recited in claim 1, wherein said arm includes a reinforcing portion.
7. An adjustable hanger as recited in claim 1, wherein said suspending means includes a hook.
8. An adjustable hanger as recited in claim 1, wherein said biasing means is a coil spring.
9. An adjustable hanger for supporting a fluid source, comprising:
    an arm formed with a suspending member, and having an opening for receiving a hanger support frame;
    a plunger having an opening alignable with said arm opening for receiving said hanger support frame;
    a biasing element interposed between said arm and said plunger for biasing said plunger in a direction along the longitudinal axis of said arm; and
    said plunger being associated with said arm for movement between an unlocked position wherein said openings are aligned to permit said arm and plunger to be adjustably moved along said hanger support frame, and a locked position wherein said biasing element urges said arm and plunger against said hanger support frame to lock said adjustable hanger in place.
10. An adjustable hanger as recited in claim 9, wherein said arm has an axial chamber and said movable plunger is coaxially movable within said chamber.
11. An adjustable hanger adapted to be slidably mounted on a hanger support frame for supporting a fluid source, comprising:
    an arm formed with a member for suspending a fluid source and an opening for slidably engaging said hanger support frame;
    a plunger formed with an opening for slidably engaging said hanger support frame, and associatd with said arm for movement between a first position wherein said arm opening and said plunger opening are aligned to permit free movement along said hanger support frame, and a second position; and
    a biasing element associated with said arm and plunger for urging said arm and plunger into said second position wherein a locking surface of said plunger opening and an inner surface of said arm opening engage said hanger support frame to clamp said adjustable hanger in place.

* * * * *